US011439785B2

(12) United States Patent
Hietala et al.

(10) Patent No.: US 11,439,785 B2
(45) Date of Patent: Sep. 13, 2022

(54) METHODS AND SYSTEMS FOR REMOVING LIQUID FROM A SAMPLE

(71) Applicant: General Electric Company, Schenectady, NY (US)

(72) Inventors: Mika Harri Juhani Hietala, Espoo (FI); Asko Saarelainen, Espoo (FI); Jarmo Luusua, Vantaa (FI)

(73) Assignee: General Electric Company, Schenectady, NY (US)

( * ) Notice: Subject to any disclaimer, the term of this patent is extended or adjusted under 35 U.S.C. 154(b) by 728 days.

(21) Appl. No.: 16/236,130

(22) Filed: Dec. 28, 2018

(65) Prior Publication Data

US 2020/0206450 A1 Jul. 2, 2020

(51) Int. Cl.
*A61M 16/08* (2006.01)
*G01N 33/00* (2006.01)
*B01D 53/26* (2006.01)

(52) U.S. Cl.
CPC ....... *A61M 16/0808* (2013.01); *B01D 53/266* (2013.01); *G01N 33/0011* (2013.01)

(58) Field of Classification Search
CPC .. A61M 16/08; G01N 33/0011; B01D 53/266
See application file for complete search history.

(56) References Cited

U.S. PATENT DOCUMENTS

| 6,342,092 B1* | 1/2002 | Lichon | B01D 19/0031 |
| | | | 210/188 |
| 7,402,197 B2* | 7/2008 | Larsen | B01D 46/0031 |
| | | | 55/394 |
| 9,861,910 B2* | 1/2018 | Hammad | B01D 53/1425 |
| 2005/0178269 A1* | 8/2005 | Weckstrom | B01D 53/22 |
| | | | 96/6 |
| 2012/0136269 A1* | 5/2012 | Weckstrom | A61M 16/0833 |
| | | | 600/532 |

* cited by examiner

*Primary Examiner* — Youngsul Jeong
(74) *Attorney, Agent, or Firm* — McCoy Russell LLP

(57) ABSTRACT

Various methods and systems are provided for removing liquid from a sample containing both liquid component and gaseous component. In particular, the liquid component may be separated from the sample by flowing the gaseous component of the sample from a lower chamber to an upper chamber through a membrane. The liquid portion of the sample may be drain from the lower chamber via a drainage channel within the bottom wall of the lower chamber. The liquid portion of the sample flows horizontally outward in the drainage channel through capillary action induced by a capillary part positioned within the drainage channel.

13 Claims, 8 Drawing Sheets

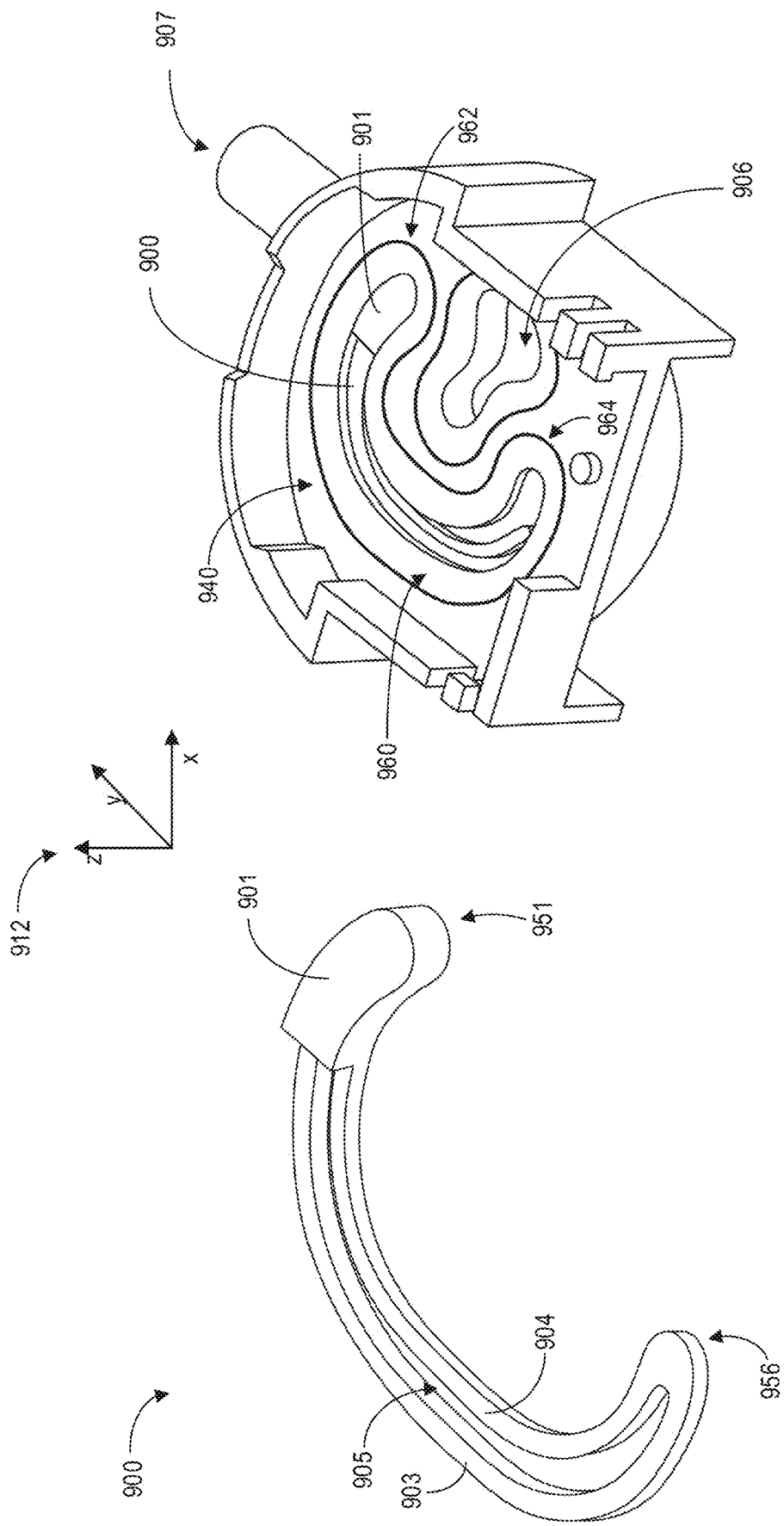

METHODS AND SYSTEMS FOR REMOVING LIQUID FROM A SAMPLE

FIELD

Embodiments of the subject matter disclosed herein relate to methods and systems for separating liquid component from a sample, and more particularly, to removing liquid component from a sample exhaled by a subject and/or provided to the subject for inhalation.

BACKGROUND

During anesthesia or in intensive care, condition of a patient may be monitored by analyzing the composition of gas (such as $CO_2$, $O_2$, $N_2O$, and anesthetic agents) inhaled and exhaled by the patient. For example, the content of the gas may be determined by a gas analyzer. However, the sample may contain liquid components such as water droplets, mucus, and blood. These liquid components need to be removed from the sample before analyzing the gaseous components of the sample.

BRIEF DESCRIPTION

In one embodiment, a method for removing liquid from a sample comprises flowing a gaseous portion of the sample from a lower chamber to an upper chamber through a membrane, and flowing a liquid portion of the sample from the lower chamber to a container via a channel in a bottom wall of the lower chamber, wherein the liquid portion of the sample flows horizontally outward in the channel by capillary action.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIG. 9A shows an example capillary part of the gas liquid separation apparatus of FIG. 2.

FIG. 9B shows an example lower chamber of a gas liquid separation chamber of the gas liquid separation apparatus of FIG. 2.

DETAILED DESCRIPTION

Figure 1:
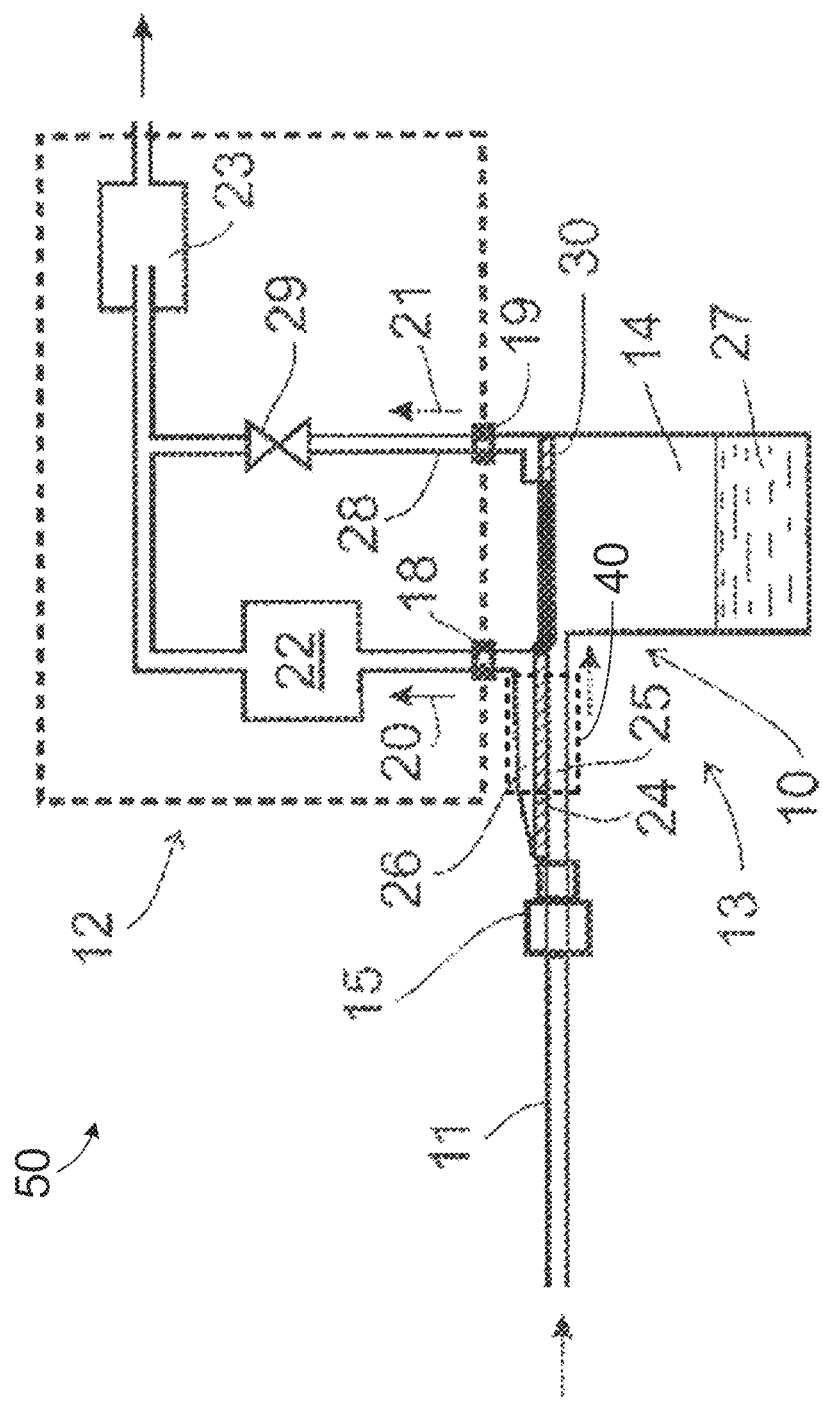
FIG. 1 illustrates an example configuration of a gas analyzer.
Figure 2:
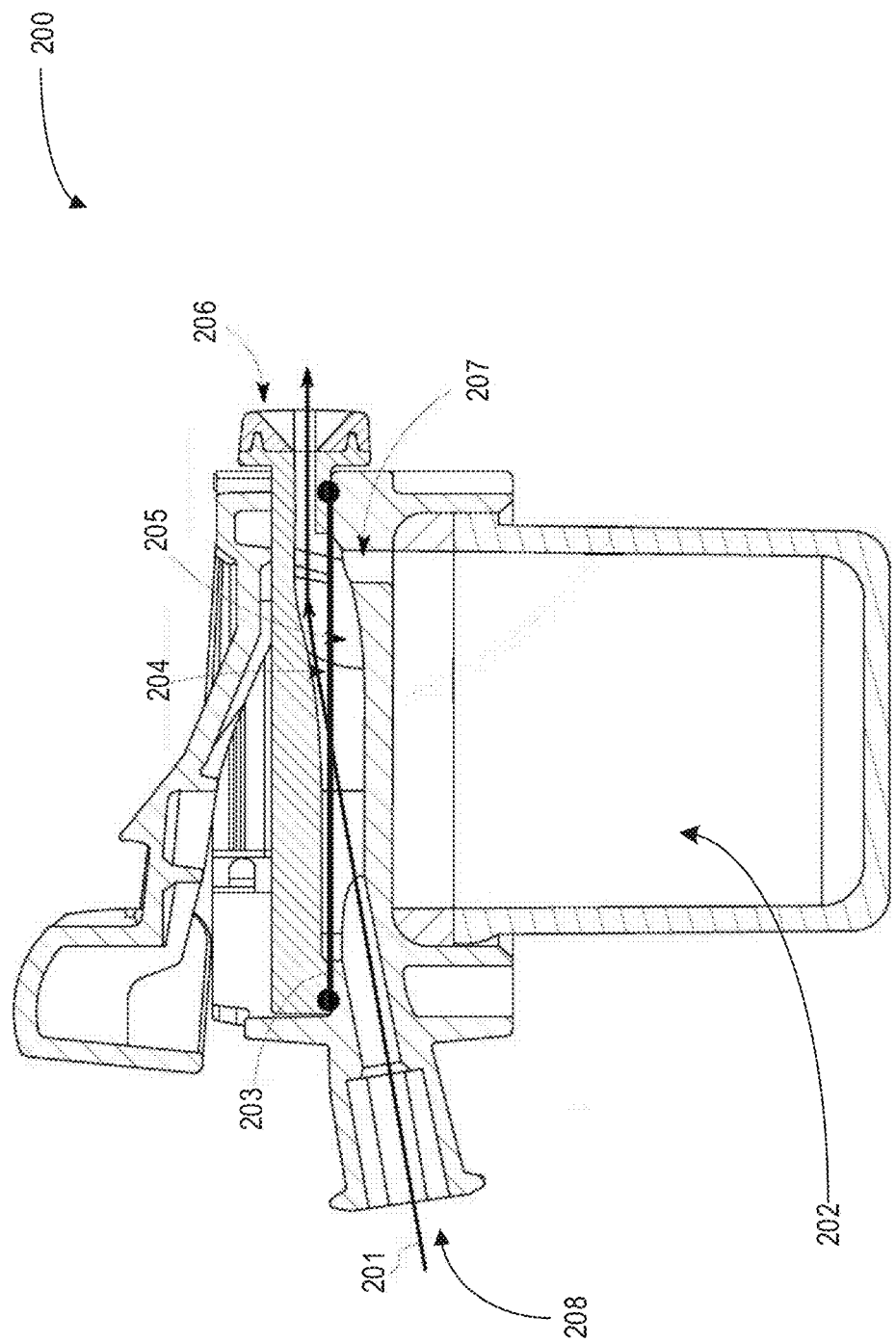
FIG. 2 shows a cross-section of a gas liquid separation apparatus of an example gas analyzer.
Figure 3:
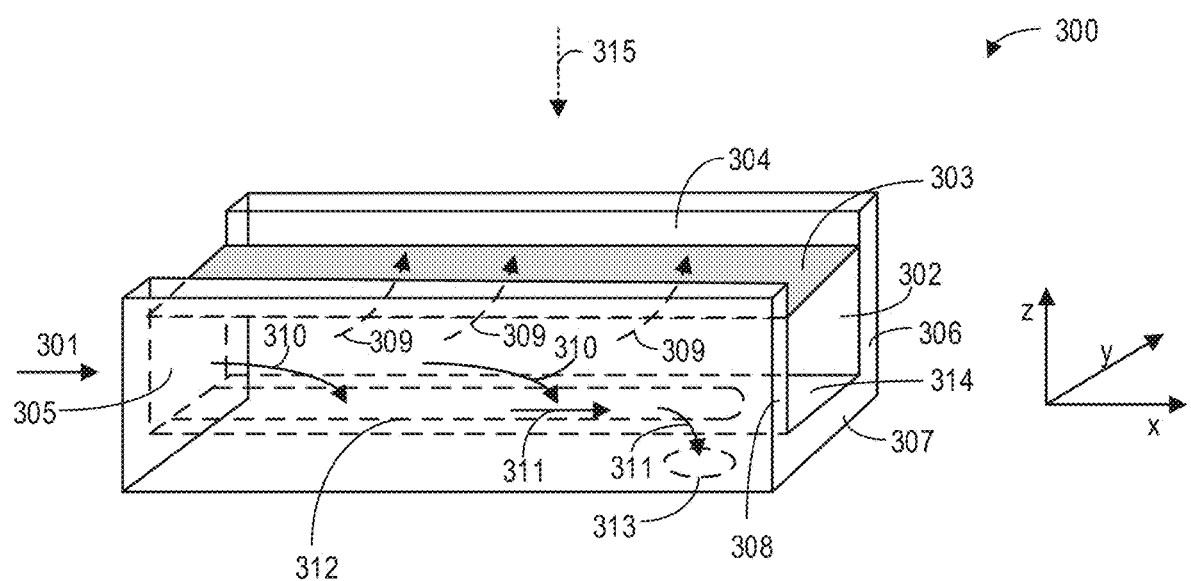
FIG. 3 shows a gas liquid separation chamber of the gas analyzer of FIG. 1, according to an embodiment.
Figure 4:
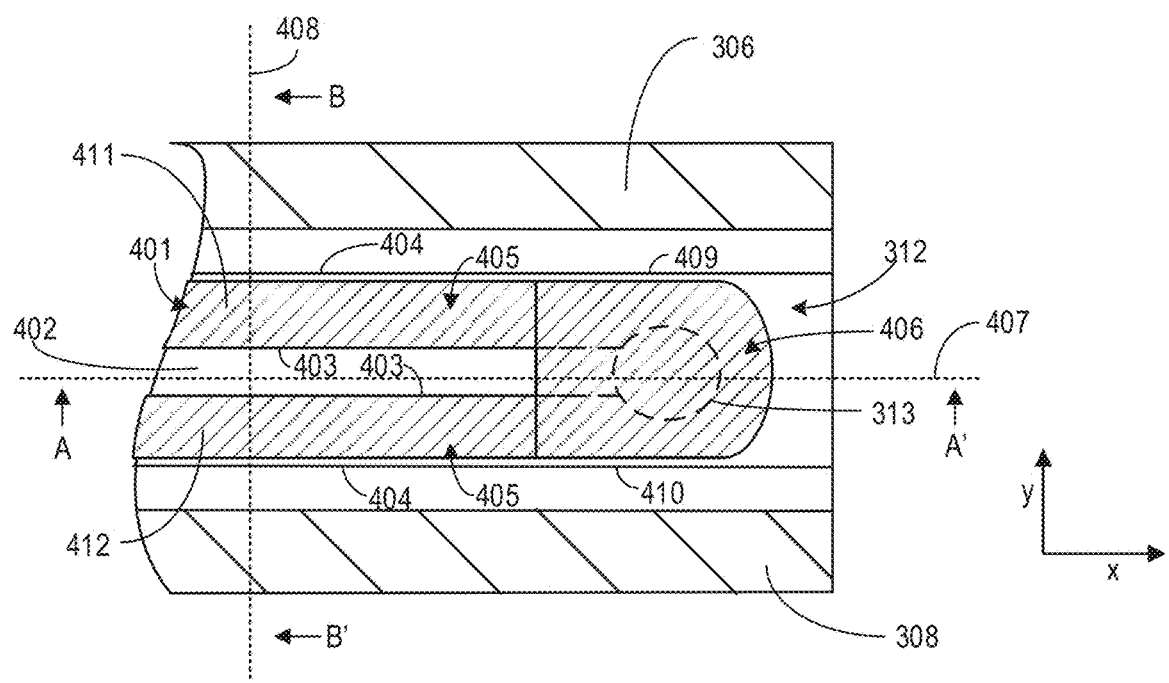
FIG. 4 is a top view of the gas liquid separation chamber of FIG. 3.
Figure 5:
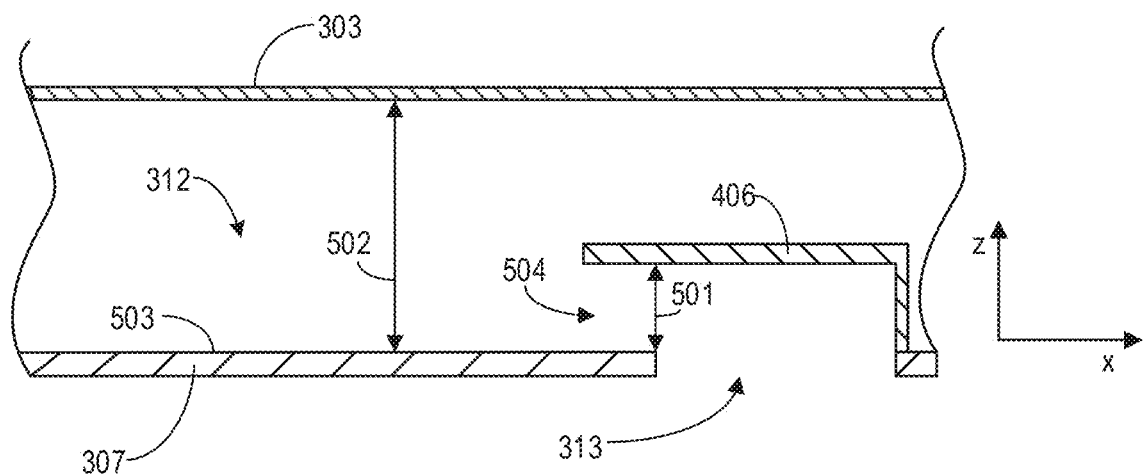
FIG. 5 shows a longitudinal cross-section of the gas liquid separation chamber of FIG. 3.
Figure 6:
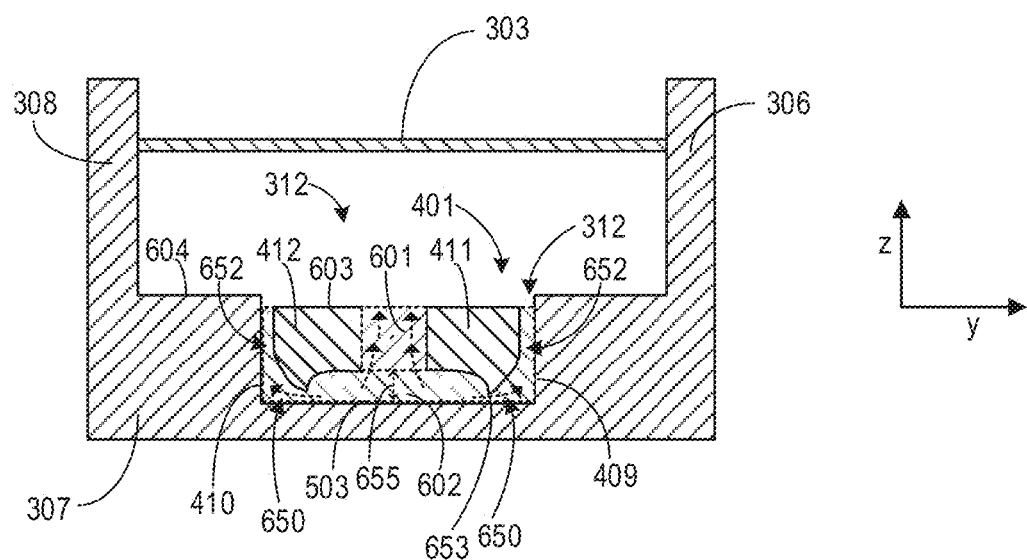
FIG. 6 shows a lateral cross-section of the gas liquid separation chamber of FIG. 3.
Figure 7:
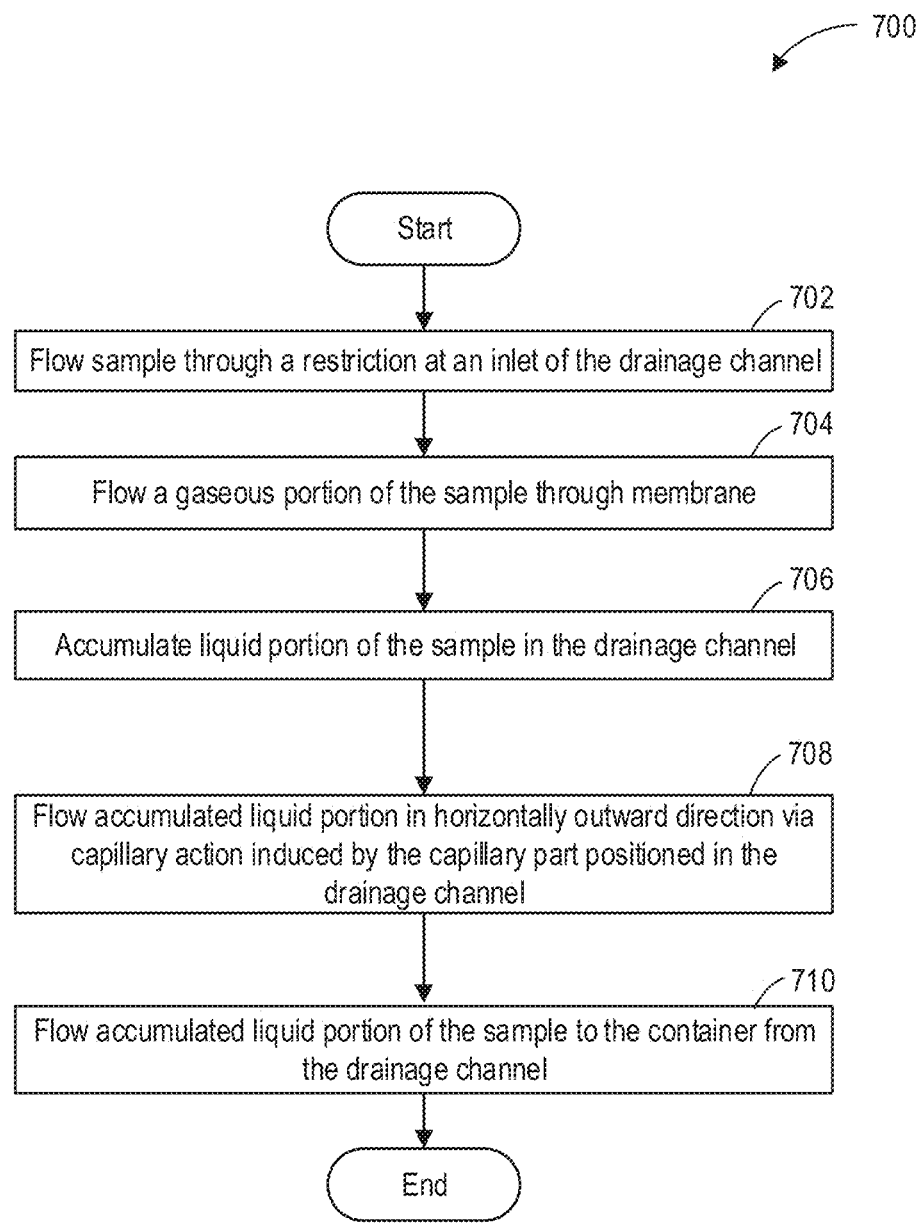
FIG. 7 shows an example method for removing liquid from a sample.
Figure 8:
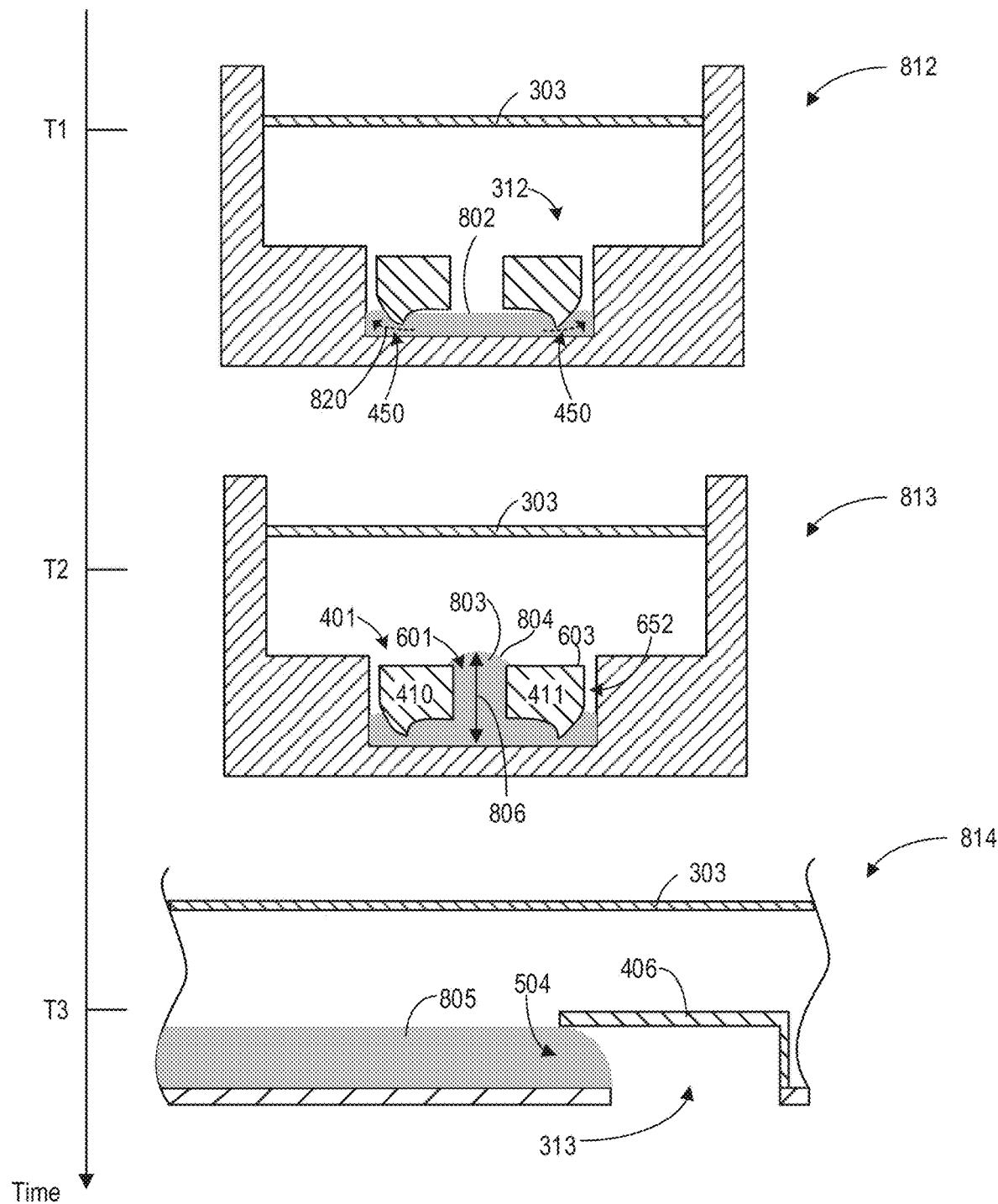
FIG. 8 illustrates locations of the liquid in the gas liquid separation chamber over time according to the method of FIG. 7.
Figure 9C:
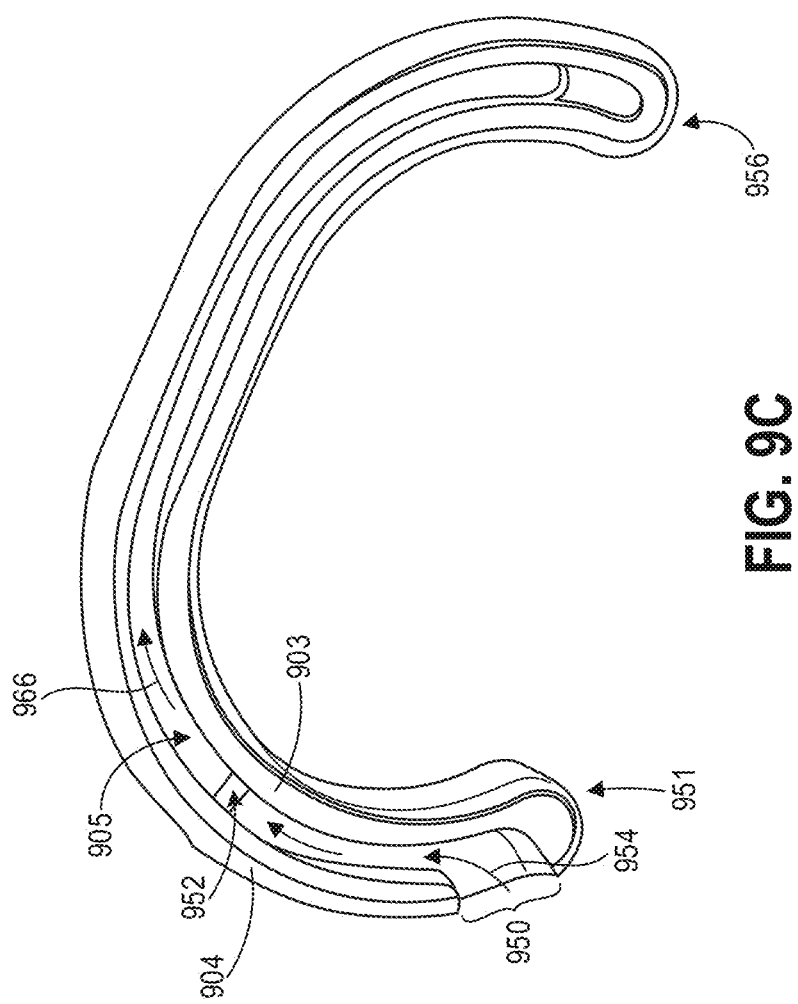
FIG. 9C shows another view of the capillary part, shown in FIG. 9A.

The following description relates to various embodiments of gas analyzer including a liquid separation apparatus for removing liquid from a sample and methods for operation of the liquid separation apparatus. The sample may be exhaled from a subject and/or provided to a subject for inhalation, and may include both liquid and gaseous content. FIG. 1 shows an example gas analyzer for analyzing the gaseous content of the sample. Before analyzing the gaseous content, liquid may be removed by passing the sample through a gas liquid separation apparatus of the gas analyzer. FIG. 2 shows a cross-section of an example gas liquid separating apparatus. The gas liquid separating apparatus may include a gas liquid separation chamber. An example configuration of the gas liquid separation chamber is shown in FIG. 3. The gas liquid separation chamber may include an upper chamber and a lower chamber separated by a membrane. The membrane only allows the gaseous portion of the sample flowing through. In some embodiments, after flowing the sample into the lower chamber, the gaseous portion of the sample passes the membrane to the upper chamber, and the liquid portion of the sample flows to a container coupled to the lower chamber. However, in previous systems, the membrane may be easily blocked by the accumulated liquid in the lower chamber, especially when the accumulated liquid at the bottom of the lower chamber is not effectively drained into the container. In order to address this issue, a drainage channel is provided at the bottom wall of the lower chamber to direct liquid to the container. The drainage channel includes a capillary insert designed to horizontally spread liquid in a drainage channel via capillary action. In sum, the capillary flow features allow the height of the liquid's top surface to be diminished to reduce the likelihood of membrane blockage by the liquid. As a result, the reliability of the gas analyzer is increased, enabling the analyzer to be operated for a longer duration. In some embodiments, the channel may be formed by positioning a capillary part in a drainage channel within the bottom wall of the lower chamber. FIG. 4 is a top view of the capillary part within the drainage. FIG. 5 shows a longitudinal cross-section of the gas liquid separation chamber. The capillary part may include a roof-like portion at an end of the capillary part, forming an opening upstream of the outlet to the container. When the accumulated liquid in the lower chamber may block the opening, a vacuum is generated in the container thereby drawing the liquid into the container. In this way, the accumulated liquid may be more effectively removed from the lower chamber. FIG. 6 shows a lateral cross-section of the liquid separation chamber. FIG. 7 is a method of separating liquid from the sample and managing the flow of the liquid using the gas liquid separation chamber shown in FIGS. 3-6. FIG. 8 illustrates locations of the accumulated liquid while implementing the method of FIG. 7. FIGS. 9A, 9B, and 9C show an example capillary part and an example lower chamber of the gas liquid separation apparatus of FIG. 2.

FIG. 1 illustrates the configuration of a gas analyzer 50. The gas analyzer includes a gas analyzing subsystem 12 with a gas liquid separation apparatus 13. The gas liquid separation apparatus 13 may comprise a housing 10, a gas liquid separation chamber 40, an inlet 15, a container 14, a first outlet 18, and a second outlet 19. The inlet 15 delivers a sample to the gas liquid separation chamber 40. The sample may include the exhalation of the subject and/or may be provided to the subject for inhalation. The sample may also include a portion of a gas delivered to the subject. The first outlet 18 and the second outlet 19 output the gaseous portion of the sample to the gas analyzing subsystem 12. The gas liquid separation chamber 40 includes an upper chamber 26 and a lower chamber 25 separated by a first membrane 24. A second membrane 30 is positioned between the container 14 and the second outlet 19. The first and the second membranes may be both hydrophobic and oleophobic, so that only gas may pass through the membranes. The gas analyzing subsystem 12 includes a pump 23 for drawing the sample flowing through the gas analyzer.

The sample enters the gas analyzer via the sampling line 11. A gaseous portion of the sample may flow through the first membrane 24 and exit the gas liquid separation apparatus 13 from the first outlet 18. The gaseous sample passed through the membrane 24 may then flow from the first outlet 18 to a gas sensor 22 (as shown by flow 20) for measuring the content of the gaseous sample flowing to the pump 23. The gas sensor 22 may comprise one or more of non-dispersive infrared (IR) sensors for detecting carbon dioxide, nitrous oxide, and anesthetic agents, such as halothane, enflurane, isoflurane, desflurane, and sevoflurane. The gas sensor 22 may also include an oxygen sensor.

The rest of the sample not passing through the membrane 24 may flow into a container 14 from the lower chamber 25 of the gas liquid separation chamber 40. The sample entering the container 14 may include both liquid and gas. The liquid portion 27 of the sample entering container 14 may accumulate at the bottom of container 14. Therefore, it will be appreciated that the liquid portion of the sample may flow from the lower chamber 25 to the container 14. The gas in container 14 may exit the container from the second outlet 19 via the second membrane 30. The gas exited the second outlet 19 may then flow to valve 29 through tube 28, as indicated by flow 21. The valve 29 controls the flow through tube 28. The gas passed valve 29 may then flow to pump 23. As such, the pump 23 may introduce vacuum in the container 14. The pump may also introduce a vacuum in the upper chamber 26 to facilitate the flow of the gaseous portion of the sample from the lower chamber 25 to the upper chamber 26.

In this way, the sample flows through the sampling line 11 and the inlet 15 into the gas liquid separation apparatus 13, which may be disposable. The gaseous portion of the sample may be separated from the liquid portion of the sample by membrane 24, and flows to the gas analyzing subsystem 12. The liquid portion of the sample is collected in the container 14.

FIG. 2 shows a cross-section of an example gas liquid separation apparatus 200. The sample flows into the apparatus 200 via the inlet 208. The liquid content of the sample is removed by filtering the sample through a membrane 203 positioned between the upper chamber 204 and lower chamber 205. The gaseous sample in the upper chamber 204 then flows outside of the apparatus 200 via the first outlet 206. The flow path of the gaseous sample exiting the first outlet is shown as 201. The first outlet may be pneumatically connected with a gas sensor for analyzing the gas content of the sample. The liquid portion of the sample, which may include a small amount of gaseous portion of the sample, is drained to the container 202 via the second outlet 207.

FIG. 3 is a three-dimensional view of an example gas liquid separation chamber 300 (similar to the gas liquid separation chamber 40 in FIG. 1) of the gas analyzer. The x-axis is the longitudinal direction, the y-axis is the lateral direction, and the z-axis is the vertical direction. Herein, "top" and "bottom" correspond to an increase and decrease in the vertical direction, respectively. The arrow in the vertical direction indicates increased height. The chamber 300 may include a lower chamber 302 and an upper chamber 304 separated by the first membrane 303. The chamber 300 is defined by side walls 306 and 308, bottom wall 307, and top wall (not shown) above the first membrane 303 in the vertical direction.

The input flow 301 of the sample enters the lower chamber 302 from inlet 305. The input flow is divided in to a first flow 309 from the lower chamber 302 to the upper chamber 304 through the membrane 303 and a second flow from the lower chamber 302 to the drainage channel 312. The drainage channel 312 may be a recess within the bottom wall 307 of chamber 300. The first flow may include only gaseous components of the input sample. The first flow may exit the upper chamber 304 via the first outlet (not shown) located in the top wall of the chamber 300. The second flow may include both gaseous components and the liquid components of the sample. The liquid components may accumulate in the channels (not shown in FIG. 3) of the drainage channel 312 and flow to the outlet 313 to the container (such as container 14 of FIG. 1), as indicated by arrows 311. In some embodiments, the side surfaces of the drainage channel may be parallel to each other. Further in some embodiments, the bottom surface of the drainage channel may be parallel to the bottom wall of the chamber 300. Additionally, in some embodiments, the bottom surface of the drainage channel may be tilted in the vertical direction to facilitate the accumulated liquid flowing to the outlet 313. However, other drainage channel contours may be used in other embodiments.

A capillary part (not shown in FIG. 3) may be positioned within the drainage channel to prevent liquid accumulation over the top surface 314 of the bottom wall 307. The position of the capillary part is shown in detail from cross-sectional views in FIGS. 4-6.

FIG. 4 is a top view of the gas liquid separation chamber 300 of FIG. 3. In particular, as shown in FIG. 3, the chamber 300 is viewed from direction 315, without the first membrane 303. The x-axis is the longitudinal direction, and the y-axis is the lateral direction. The drainage channel 312 is illustrated with a capillary part 401. The capillary part 401 is designed to spread the liquid out in the drainage channel to reduce the vertical height of the liquid. Consequently, the likelihood of membrane blockage caused by liquid interference is reduced.

The capillary part 401 is positioned within the drainage channel 312. In one embodiment, the side surfaces 409 and 410 of the drainage channel 312 may be parallel with each other. However, other side surface contours may be used in other embodiments. The capillary part 401 extends along the drainage channel 312 from a first end of the channel to a second end of the channel. Walls 411 and 412 of the capillary part 401 define boundaries of capillary sections and a middle flow section 402. The second portion forms a roof-like cover on top of the outlet 313. The capillary part 401 may be made from plastic, metal, or other suitable solid materials. Middle flow section 402 is formed around the capillary part within the drainage. The middle flow section 402 may extend along the drainage, and is in fluid connection with the outlet 313 below the capillary part 401 in the vertical direction. The liquid portion of the sample may accumulate within the middle flow section 402, and flow towards the second outlet along the drainage channel. However, it will be appreciated that, prior to liquid flowing through the middle flow section, the liquid may flow along outer walls of the drainage channel due to the flow dynamics generated by the capillary part.

The middle flow section 402 extends along the bottom wall of the lower chamber. Surfaces 403 of the walls 411 and 412 define peripheral boundaries of the middle flow section 402. The liquid may enter the channel via an inlet with a restriction 952, shown in FIG. 9C. Continuing with FIG. 4, when the liquid is in the flow channel the capillary part 401 horizontally forces the liquid to horizontal walls of the drainage channel to reduce the height the liquid. It will be appreciated that the liquid may flow out of the drainage channel 312 through the outlet 313 into the container 202, shown in FIG. 2. The horizontal width of the middle flow section 402 (i.e., horizontal distance between surfaces 403) may be in a range between 0.5-1.5 mm. However, numerous suitable width dimensions have been contemplated. FIG. 4 also shows side walls 404 of the drainage channel 312. In the illustrated embodiment, the side walls 404 are parallel to each other. In another embodiment, the side walls 404 may not be parallel to each other. For example, the side walls 404 of the upstream portion may converge or diverge along the lengths of the walls.

It will be appreciated that in one example, the capillary part 401 may be manufactured in an integrated manner with the drainage channel 312. That is to say, the capillary part and the drainage channel is made out of a continuous piece of material. However, in the illustrated embodiment the capillary part 401 is a designed as an insert for the drainage channel 312.

FIG. 5 shows a longitudinal cross-section of the gas liquid separation chamber including plane 407, viewed in the A-A' direction, as shown in FIG. 4. The longitudinal cross-section is within the x-z plane. The wall 406 of the capillary part 401 is positioned at least partially over the outlet 313 with regard to the vertical direction z. The wall 406 of the capillary part and the bottom surface 503 of the drainage channel 312, together with the walls 411 and 412 of the capillary part 401, shown in FIG. 4, form an opening 504 upstream of the outlet 313. The lateral cross-sectional area of the opening 504 may be less than 2.0 mm, in one example. Further, in one example, the lateral cross-sectional area of the opening 504 may be smaller than the combined upstream and downstream cross-sectional areas. However, openings with other sizes have been envisioned. In one example, the height 501 of the wall 406 from the bottom surface 503 of the drainage channel 312 is less than 1.0 mm. In another example, the height 502 of the first membrane 303 from the bottom surface 503 of the drainage is over 2.0 mm. However, other dimensions of the drainage channel have been contemplated.

FIG. 6 shows a lateral cross-section of the gas liquid separation chamber along plane 408, viewed in the B-B' direction, as shown in FIG. 4. The lateral cross-section is within the y-z plane. The capillary part 401 is positioned within the drainage channel 312. The capillary part 401 is shown spaced away from the bottom surface 503 of the drainage channel 312 and the side surface 409, 410 of the drainage channel. The top surface 603 of the capillary part 401 may be vertically lower than the top surface 604 of the bottom wall 307 of the gas liquid separation chamber in the vertical direction. However, in other examples, the capillary part 401 may have a similar height to the bottom wall 307 or extend above the bottom wall. The middle flow section 402 of the capillary part 401 is shown in FIG. 6. However in other examples, the middle flow section may be omitted from the capillary part. The middle flow section 402 is arranged between the two walls 411 and 412 of the capillary part 401. In some examples, the distance between the two walls 411 and 412 may be greater than the distance between the capillary part and the surface of the drainage. In one specific example, the distance between the two walls 411 and 412 may be greater than 0.5 mm. However, other dimensions of the capillary part walls have been envisioned. The walls 411 and 412 define boundaries of various flow sections in the drainage channel. Specifically, the walls 411 delineate horizontal capillary sections 650 and vertically capillary sections 652 of the drainage channel. The horizontal capillary sections 650 extend horizontally away from a central axis 655 of the drainage channel 312, in the depicted example. The width of the capillary sections 650 may be less than 1.0 mm, in one example. However, other dimensions may be used, in other examples. The capillary sections of the drainage channel function to spread (e.g., horizontally spread) the liquid out in the drainage channel to reduce the height of the liquid. The general flow of liquid through the capillary sections is indicated via arrows 653. In this way, the likelihood of the liquid contacting the membrane positioned above the drainage channel is reduced. It will be appreciated that the membrane may be hydrophobic and oleophobic but would be blocked by liquid if it hits the membrane. Thus, spreading the liquid flow via capillary action reduces the chance of membrane blockage.

The boundary of capillary sections 6501 and 652 is also bounded by side surfaces 409 and 410 of the drainage channel 312.

FIG. 7 shows an example method 700 for removing liquid from a sample using the gas liquid separation chamber shown in FIGS. 1-6. In particular, some gaseous components of the sample may first flow into the channel while droplets of the liquid components of the sample accumulate in the drainage channel. The accumulated liquid may be spread outward in the drainage channel via capillary action induced by the capillary part. The accumulated liquid may simultaneously flow along the channel to an opening draining into the container. Furthermore, once the accumulated liquid blocks the opening of the capillary part, a vacuum may be generated in the container, thereby promoting liquid flow into the container.

FIG. 8 illustrates the flow of the liquid sample relative to the channel over time. In FIG. 8, time increases as indicated by the arrow of the time axis. Plots 812-813 are the same lateral cross-section of the gas liquid separation chamber shown in FIG. 6. Plot 814 is the same longitudinal cross-section of the gas liquid separation chamber shown in FIG. 5. The same components are indicated by the same numerical number.

At 702, the sample flows through a restriction at the inlet of the drainage channel. The restriction is designed to regulate the amount of liquid entering the drainage channel. The sample may be drawn to the lower chamber by operating a pump (such as pump 23 of FIG. 1) downstream of the gas liquid separation chamber. In this way, liquid is introduced into the channel along the bottom of the channel. However, other mechanisms for driving sample flow into the lower chamber have been contemplated.

At 704, a gaseous portion of the sample flows through the membrane (such as membrane 303 of FIG. 3) to the upper chamber from the lower chamber. In this way, gas which has reduced moisture content may be flowed into an upper chamber which may be design to flow the gas to a sensor, for example.

At 706, the liquid portion of the sample is accumulated in the drainage channel. Specifically in one example, the liquid sample that has been introduced into the channel along the bottom of the channel first propagates along the side walls of the drainage channel followed by the bottom portion below the capillary part in the channel and the travels downstream to the outlet opening.

As shown in plot 812 of FIG. 8, at time T1, the accumulated liquid 802 is accumulated in the drainage channel (such as the downstream portion 602 of FIG. 6).

At 708, the accumulated liquid portion is flowed horizontally outward via capillary action induced by the capillary part positioned in the drainage channel. As, shown in plot 812 of FIG. 8, at time T1, the accumulated liquid 802 travels through horizontal capillary sections 450, indicated via arrows 820, of the drainage channel 312. In some examples, liquid flow through the vertical capillary sections 652 caused by capillary action may also occur at step 708.

It will be appreciated that the liquid may continue to accumulate in the drainage channel. As the amount of accumulated liquid increases, the middle flow section of the channel may be filled with liquid. Thus, as shown in plot 813 of FIG. 8, at time T2, the amount of accumulated liquid 802 is increasing, and starts filling the middle flow section 601. Due to the cohesion and adhesion forces among the water molecules, the liquid travels into the middle flow section 601. These forces also reduce the likelihood of the liquid flowing onto the top surface 603 of the walls 410 and 411 of the capillary part 401. In this way, the height 806 of the top surface 804 of the accumulate liquid 803 is decreased to reduce the likelihood of liquid interference with the membrane 303. For example, the height of the liquid may be less than the height from the bottom of the membrane 303. Therefore, the accumulated liquid may be essentially kept away from the membrane 303, so that the possibility of membrane blocking is reduced.

At 710, the accumulated liquid from the sample is flowed into the container from the drainage channel. As shown in plot 814 of FIG. 8, at time T3, the accumulated liquid 805 flows through the opening 504. In turn, the liquid may be flowed from the opening 504 to the outlet 313 coupled to the container. In this way, accumulated liquid may be directed to the container from the drainage channel 312. It will be appreciated that when the liquid blocks the opening 504 a vacuum may be generated in the container due to the gas exiting the container. The vacuum will therefore draw liquid into the container. As such, the liquid is efficiently flowed into the container from the drainage passage.

In this way, by limiting the height of the accumulated liquid in the lower chamber, the possibility for the accumulated liquid blocking the membrane is decreased.

FIG. 9A shows another embodiment of the capillary part 900 in a lower chamber 940. The capillary part 900 is curved in a C-shape, in the illustrated example. However, other capillary part contours have been envisioned. The capillary part 900 includes walls 903 and 904. The walls 903 and 904 define the boundaries of the capillary sections and the middle flow section 905 of the drainage channel in which the capillary part 900 is positioned.

The sample may be introduced into capillary part 900 through an inlet 950 and then through a restriction 952, shown in FIG. 9C. The restriction decreases a cross-sectional area of the drainage channel with regard to downstream flow. Specifically, the restriction is positioned between walls 903 and 904 and extends in a vertical direction. However, other restriction contours may be used in other embodiments. The inlet 950 is positioned at a first end 951 of the capillary part 900. The restriction 952 opens into the middle flow section 905. Arrows 954 depict the general direction of liquid flow into the capillary part 900 through the inlet 950. The inlet 950 is shown positioned below surface 901, shown in FIG. 9A. However, other positions of the inlet 950 have been contemplated.

FIG. 9B shows an inlet channel 907 coupled to the inlet 950 of the capillary part 900. Thus, the sample may be flowed through the inlet channel 907 and into the drainage channel 960 via the inlet 950.

FIG. 9B also shows the capillary part 900 extending from a first end 962 of the drainage channel 960 and the second end 964 of the drainage channel 960.

It will be appreciated that liquid flows through the middle flow section 905 and then to an outlet positioned below a second end 956 of the capillary part 900. The outlet may drain into a container, such as the container 202, shown in FIG. 2. Therefore, liquid may be introduced into the drainage channel 960 and then travel along the channel in a general direction indicated via arrow 966, shown in FIG. 9C. It will be appreciated that liquid may flow first through horizontal and/or vertical capillary sections of the capillary part 900, due to the capillary action, then subsequently fill up and flow through the middle flow section 905. In this way, the liquid flow along the drainage channel is spread out via capillary action to reduce the height of the liquid.

Continuing with FIG. 9B showing a gas outlet channel 906. The gas flow outlet channel allows gases to exit the container. Thus, the gas outlet channel 906 opens into the container. The gas outlet channel 906 therefore allows gas to flow out of the container to decrease container pressure when the container inlet is blocked by the liquid.

It will be appreciated that at least a portion of the components (e.g., the drainage channel, capillary part, lower chamber, etc.,) shown in FIGS. 9A-9C may be parts of the gas liquid analyze apparatus 200 of FIG. 2.

The gas analyzer with the gas liquid separation chamber described herein effectively removes liquid components of the sample flowing into the gas analyzer, while at the same time reduced the chances of (e.g., prevents) accumulated liquid touching the membrane. In particular, the channel in the bottom wall of the lower chamber may drain the liquid out of the chamber, and a capillary part functions to spread the liquid in the channel through capillary action to reduce liquid height. Thus, the membrane of the chamber is less likely to be blocked by the liquid, and the gas liquid separation chamber's life span may be extended.

FIGS. 1-9C show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

The technical effect of the channel within the bottom wall of the lower chamber is to drain the liquid from the lower chamber to the channel by capillary action. Further, the channel may prevent the accumulated liquid touching the membrane and reduces the total height of the gas liquid separation chamber. The technical effect of forming a small opening at a distal end of the capillary part on top of the second outlet of the gas liquid separation chamber is increasing the possibility for the accumulated liquid to block the opening, so that the vacuum in the container can effectively drain the accumulated liquid into the container.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc., are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for removing liquid from a sample, comprising:

flowing a gaseous portion of the sample from a lower chamber to an upper chamber through a membrane; and flowing a liquid portion of the sample from the lower chamber to a container via a drainage channel in a bottom wall of the lower chamber, the drainage channel including a first capillary section of a capillary part;

wherein the liquid portion of the sample is forced to horizontal sides of the drainage channel via capillary action generated by the first capillary section.

2. The method of claim 1, wherein the drainage channel includes a second capillary section of the capillary part and wherein the first and second capillary sections extend horizontally away from a center of the drainage channel.

3. The method of claim 2, wherein the drainage channel includes a third and fourth capillary section of the capillary part extending in a vertical direction.

4. The method of claim 1, wherein the capillary part includes two walls horizontally positioned on opposing sides of a middle flow section of the drainage channel.

5. The method of claim 1, further comprising flowing the sample into the drainage channel through an inlet positioned in a lower portion of the drainage channel.

6. The method of claim 5, wherein the capillary part extends from a first end of the drainage channel to a second end of the drainage channel.

7. The method of claim 1, wherein the sample includes gas slated for inhalation by a patient and/or gas exhaled by the patient.

8. The method of claim 1, wherein the first capillary section extends below a wall of the capillary part.

9. A method for removing liquid from a sample, comprising:

flowing the sample into a drainage channel, and flowing a first gaseous portion of the sample from a lower chamber to a container while a liquid portion of the sample accumulates in the drainage channel within a bottom wall of the lower chamber;

flowing a portion of the liquid in the drainage channel horizontally outward through a plurality of capillary sections of a capillary part; and flowing a gaseous portion of the sample from the lower chamber to an upper chamber through a membrane.

10. The method of claim 9, wherein the plurality of capillary sections include horizontal capillary sections and vertical capillary sections.

11. The method of claim 9, wherein the drainage channel includes a middle flow section positioned horizontally between a first and a second capillary section included in the plurality of capillary sections.

12. The method of claim 9, further comprising flowing the liquid from the drainage channel into the container through an outlet, wherein the capillary part includes a wall at least partially extending over the outlet with regard to a vertical direction.

13. The method of claim 9, wherein the drainage channel includes a restriction at an inlet where the first gaseous portion of the sample is introduced into the drainage channel.

* * * * *